Aug. 4, 1964 H. B. LEWIS ETAL Plant Pat. 2,432
AZALEA PLANT
Filed Feb. 25, 1963 2 Sheets-Sheet 1
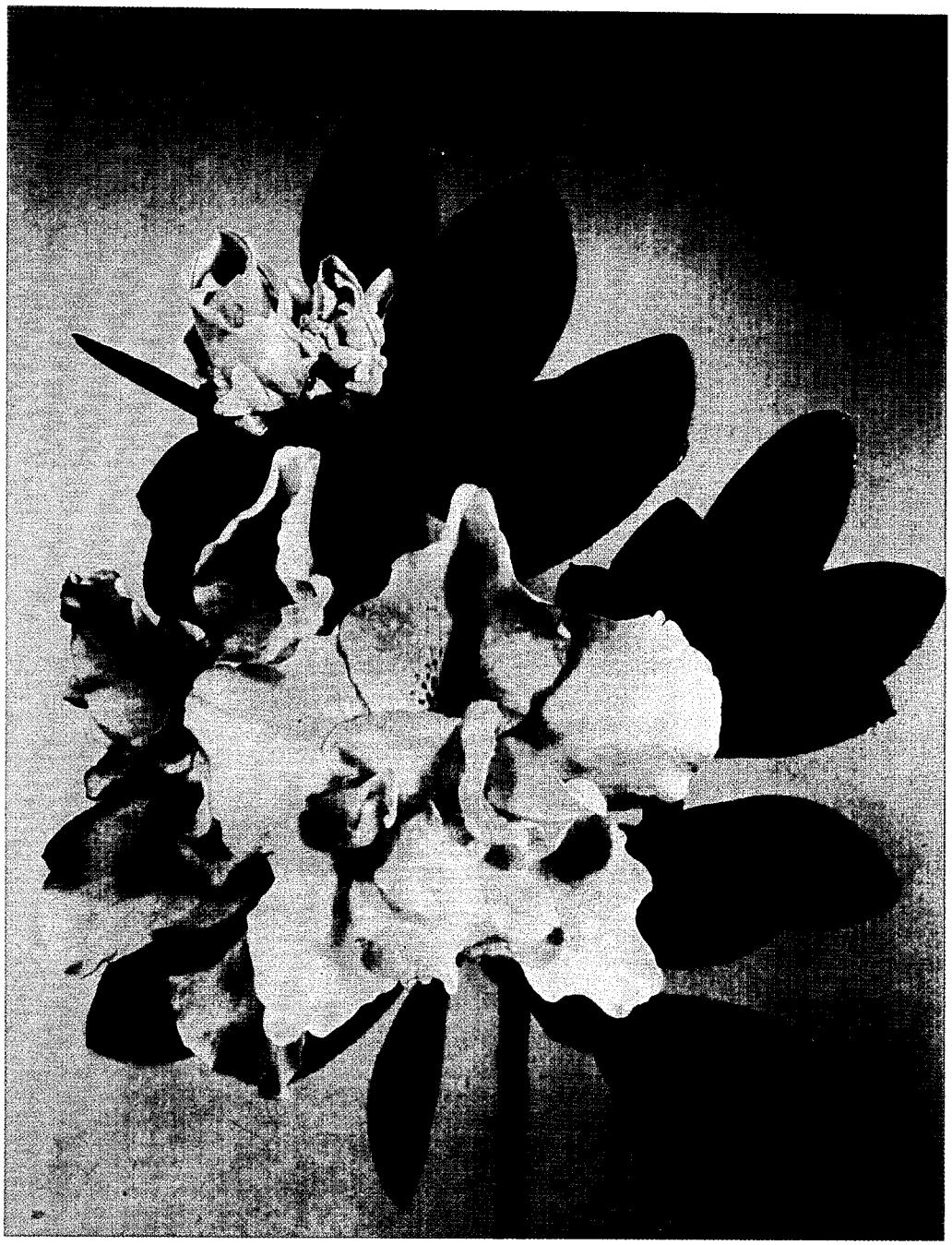
Inventors.
H. B. Lewis and
H. H. Lewis
By: Robb & Robb
Attorneys.

AZALEA PLANT
Filed Feb. 25, 1963 2 Sheets-Sheet 2
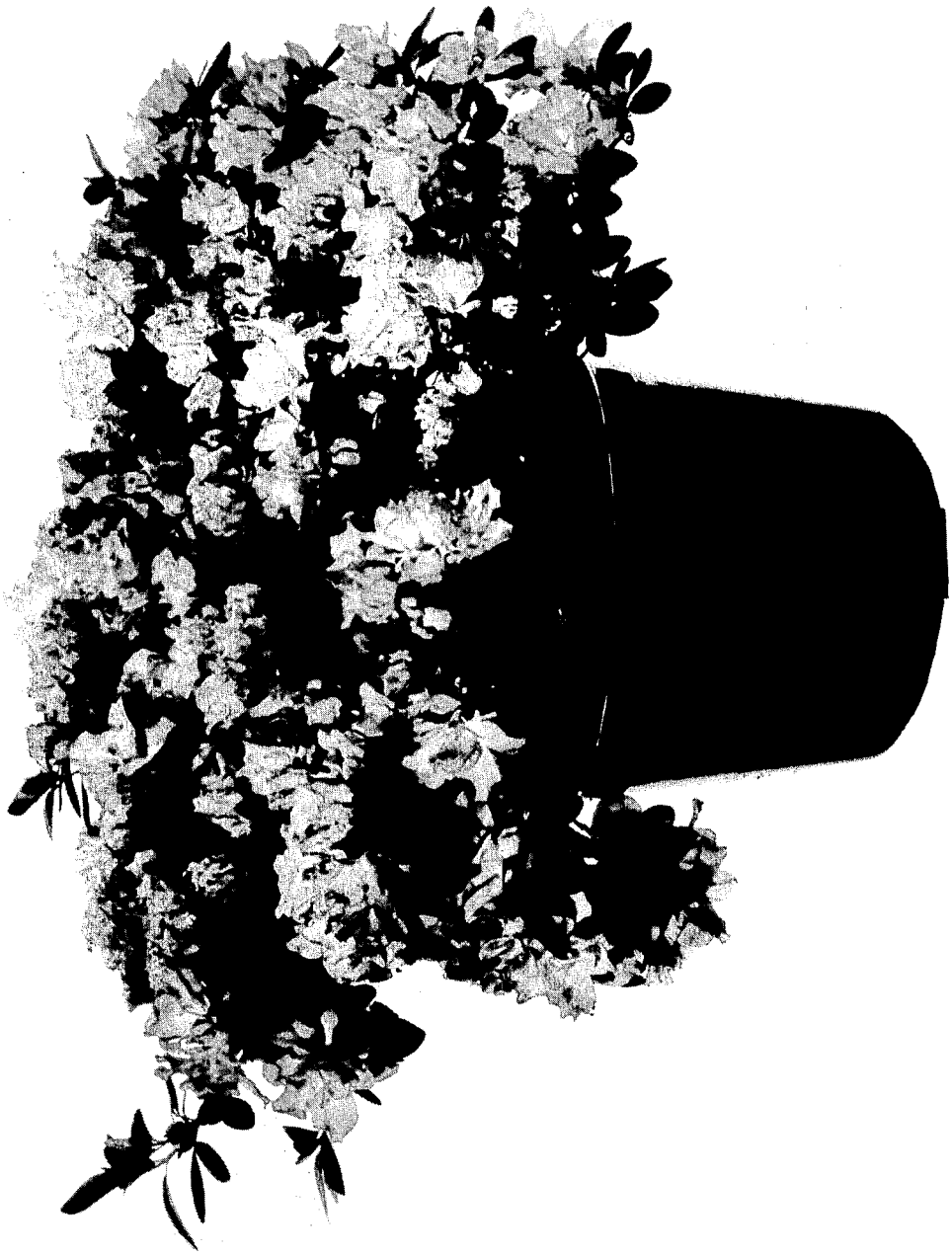
Inventors.
H. B. Lewis and
H. H. Lewis
By: Robb & Robb
Attorneys.

United States Patent Office

Plant Pat. 2,432
Patented Aug. 4, 1964

2,432
AZALEA PLANT

Hubert B. Lewis and Helen H. Lewis, both of 16562 E. Leffingwell Road, Whittier, Calif.

Filed Feb. 25, 1963, Ser. No. 269,933
1 Claim. (Cl. Plt.—56)

The present invention relates to a new and distinct variety of azalea plant which was originated by us by crossing the Belgian Indica variety known as "Dr. Bergman" (unpatented) with an unnamed and unpatented azalea variety of unknown origin and identity, the former being the seed parent and the latter being the pollen parent.

As the result of this breeding, we have produced a new azalea variety which is endowed with a new and improved combination of characteristics, as evidenced by the following features which are outstanding therein and which distinguish the new variety from its parents, as well as from all other varities of which we are aware:

(1) Medium size, flat and attractive dark green foliage;

(2) A habit of bearing flowers in clusters of from 2 to 6 flowers on short stems, each cluster giving the appearance of a single, very large double flower; and (3) A distinctive and attractive Neyron Rose general color tonality of the flowers.

In comparison with its parents, there is no resemblance of the new variety to the seed parent by virtue of the fact that the leaves of the new variety are much larger, are of an entirely different shade of green color, and the flower color is quite different, while the leaves are not smooth as those of either parent variety and are very flat.

Asexual reproduction of our new variety by cuttings, as performed at Rivera, California, and at Whittier, California, shows that the foregoing characteristics and distinctions come true to form and are established and transmitted through succeeding propagations.

The accompanying drawings show a typical specimen plant of our new azalea variety as depicted in black and white to illustrate its general form and habit of growth, as well as typical specimens of the flowers and foliage as depicted in color on a somewhat enlarged scale to better illustrate the details thereof.

The following is a detailed description of our new azalea variety, with color terminology in accordance with the Wilson Horticultural Color Chart, except where general color terms of ordinary dictionary significance are obvious:

Locality where grown and observed: Whittier, California.
Propagation: Holds its distinguishing characteristics through succeeding propagations by cuttings.

*Plant*

Habit: Medium growth; well-branched; compact; attains growth up to 3 feet tall under garden conditions.
Rooting habit: Fair from cuttings.
Foliage:

*Size.*—Medium; average length 1¾ inches; average with ⅞ inch.
*Quantity.*—Normal.
*Color.*—New foilage: upper side—Spinach Green, Plate 0960/1; under side—Scheele's Green, Plate 860/1. Old foliage: upper side—Spinach Green, Plate 0960; under side—Spinach Green, Plate 0960/3.
*Shape.*—Elliptic.
*Aspect.*—Glossy; nearly smooth.
*Disease resistance.*—Good resistance to ordinary diseases to which azalea plants are normally subject, as determined by comparison with other varieties grown under the same cultural conditions at Whittier, California.

*Flowers*

Size: Average about 3 inches in diameter.
Borne: From 2 to 6 to stem; in clusters; on short stems.
Blooming habit: Good; clusters of from 2 to 6 flowers give the appearance of one large double flower.
Blooming season: From Christmas through spring with proper pruning; good for forcing.
Quantity of bloom: Abundant, both outdoors and in greenhouse.
Continuity: One season. Keeping quality—good.
Petalage: Under normal conditions, outer hose has 5 petals and inner hose has 5 petals, with tufted center.
*Color.*—Neyron Rose, Plate 623/3, with darker edging Neyron Rose, Plate 623, and with dots on base of petals corresponding to Phlox Pink, Plate 625/1.
*Texture.*—Crisp.
*Appearance.*—Inside—consistent color. Outside—consistent color.
*Shape.*—Back hose has rather short serrated petals, with inner hose offset and covering outer hose; inner hose quite wavy with tufted center.
Bud: Color—Neyron Rose, Plate 623/3.

*Reproductive Organs*

Stamens: From 2 to 5 in number; some attached to petals. Color—yellow.
Pollen: Sparse. Color—white.
Styles: Some are well developed, while others are split.
Ovaries: Normal.

We claim:

A new and distinct variety of azalea plant, substantially as herein shown and described, characterized particularly as to novelty by the unique combination of relatively large, flat and attractive dark green foliage, a habit of bearing flowers in clusters of from 2 to 6 flowers on short stems, with each cluster giving the effect of a single, very large double flower, and a distinctive and attractive Neyron Rose general color tonality of the flowers.

No references cited.